United States Patent
Yang et al.

(10) Patent No.: US 10,152,783 B2
(45) Date of Patent: Dec. 11, 2018

(54) METHOD AND SYSTEM FOR TWO DIMENSIONAL SEDIMENT PARTICLE SHAPE CHARACTERIZATION BASED ON BOREHOLE IMAGE

(71) Applicant: Schlumberger Technology Corporation, Sugar Land, TX (US)

(72) Inventors: Shiduo Yang, Clamart (FR); Isabelle Le Nir, Clamart (FR); Kang Wang, Beijing (CN)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 52 days.

(21) Appl. No.: 15/345,602

(22) Filed: Nov. 8, 2016

(65) Prior Publication Data
US 2017/0178313 A1 Jun. 22, 2017

(30) Foreign Application Priority Data
Dec. 18, 2015 (EP) .................................... 15290324

(51) Int. Cl.
*G06K 9/00* (2006.01)
*G06T 7/00* (2017.01)
(Continued)

(52) U.S. Cl.
CPC ....... *G06T 7/0004* (2013.01); *G01N 15/1463* (2013.01); *G01V 3/30* (2013.01); *G01V 99/005* (2013.01); *G06K 9/6267* (2013.01); *H04N 7/183* (2013.01); *G01N 2015/1087* (2013.01); *G01N 2015/1093* (2013.01); *H04N 2005/2255* (2013.01)

(58) Field of Classification Search
None
See application file for complete search history.

(56) References Cited

U.S. PATENT DOCUMENTS

| 4,868,883 A | 9/1989 | Chen |
| 5,809,163 A | 9/1998 | Delhomme et al. |

(Continued)

FOREIGN PATENT DOCUMENTS

| EP | 2110688 A1 | 10/2009 |
| WO | 2014200996 A2 | 12/2014 |

OTHER PUBLICATIONS

Heckbert, P. S., & Garland, M. (1997). Survey of polygonal surface simplification algorithms. Carnegie-Mellon Univ Pittsburgh PA School of Computer Science, May 1, 1997 (31 pages).

(Continued)

*Primary Examiner* — Vikkram Bali
(74) *Attorney, Agent, or Firm* — Michael Dae

(57) ABSTRACT

In one embodiment, a method includes obtaining a borehole image deriving from a downhole tool in a wellbore of a geological formation, identifying one or more patches that correspond to sediment particles on the fullbore image, computing one or more characteristics for each of the one or more patches. The one or more characteristics may include long/short axis length, size, roundness, sphericity, orientation, or some combination thereof. The method may also include displaying a visual representation for each of the one or more characteristics.

19 Claims, 8 Drawing Sheets

(51) Int. Cl.
*G01N 15/14* (2006.01)
*G06K 9/62* (2006.01)
*H04N 7/18* (2006.01)
*G01V 3/30* (2006.01)
*G01V 99/00* (2009.01)
*G01N 15/10* (2006.01)
*H04N 5/225* (2006.01)

(56) References Cited

U.S. PATENT DOCUMENTS

| | | | |
|---|---|---|---|
| 6,272,232 | B1 | 8/2001 | Delhomme et al. |
| 7,062,072 | B2* | 6/2006 | Anxionnaz ......... E21B 47/0002 348/85 |
| 2012/0029828 | A1* | 2/2012 | Pepper .................. G01V 1/301 702/16 |
| 2015/0241591 | A1* | 8/2015 | Burmester ............... G01V 3/20 702/7 |
| 2016/0130930 | A1* | 5/2016 | Gelman ................. G01V 11/00 382/109 |

OTHER PUBLICATIONS

Luebke, D. P. (2001). A developer's survey of polygonal simplification algorithms. Computer Graphics and Applications, IEEE, 21(3), 24-35.

Douglas, David H, and Thomas K Peucker. 1973. "Algorithms for the Reduction of the Number of Points Required to Represent a Digitized Line or Its Caricature." Cartographica: The International Journal for Geographic Information and Geovisualization 10 (2). UT Press: 112-22.

Ramer, Urs. 1972. "An Iterative Procedure for the Polygonal Approximation of Plane Curves." Computer Graphics and Image Processing 1 (3). Elsevier: 244-56.

Godfried Toussaint 1983, "Solving geometric problems with the rotating calipers" in Proc. IEEE MELECON'83, Athens, Greece, May 1983 (8 pages).

Hormoz Pirzadeh, Computation Geometry with the Rotating Calipers, School of computer science, McGill University, Montreal, Canada, May 1999 (133 pages).

Cox, E.A. 1927, A method for assigning numerical and percentage values to the degree of roundness of sand grains. J. Paleontol., 1, 179-183.

Lei Wu et al: "EW-Trending uplifts along the southern side of the central segment of the Altyn Tagh Fault, NW China: Insight into the rising mechanism of the Altyn Mountain during the Cenozoic", Science China Earth Sciences, SP Science China Press, Heidelberg, vol. 55, No. 6, Apr. 11, 2012, pp. 926-939.

Extended European Search Report issued in the related EP Application 15290324.1, dated Jun. 16, 2016 (11 pages).

\* cited by examiner

METHOD AND SYSTEM FOR TWO DIMENSIONAL SEDIMENT PARTICLE SHAPE CHARACTERIZATION BASED ON BOREHOLE IMAGE

CROSS-REFERENCE TO RELATED APPLICATIONS

The present invention claims the benefits of European Patent Application No. 15290324.1, filed on Dec. 18, 2015, titled "Method and System for Two Dimensional Sediment Particle Shape Characterization Based on Borehole Image," the entire content of which is hereby incorporated by reference into the current application.

BACKGROUND

This disclosure relates to a method and system for two dimensional sediment particle shape characterization based on a borehole image.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Wells are generally drilled into a surface (land-based) location or ocean bed to recover natural deposits of oil and natural gas, as well as other natural resources that are trapped in geological formations. A well may be drilled using a drill bit attached to the lower end of a "drill string," which includes a drill-pipe, a bottom hole assembly, and other components that facilitate turning the drill bit to create a borehole. For oil and gas exploration and/or monitoring, it may be desirable to obtain information about the subsurface formations that are penetrated by a borehole for analysis. For example, sediment particle shape analysis may provide fundamental information for hydrodynamic condition and depositional environment interpretation. The spiral distribution of sediment particles provides useful information on reservoir quality evaluation. Some processes of sediment particle shape analysis may be performed via lab testing on rock samples from cores. Such processes may be inefficient and/or costly due to retrieval and transportation of the core sample, analysis of the core sample, or the like.

SUMMARY

This summary is provided to introduce a selection of concepts that are further described below in the detailed description. This summary is not intended to identify key or essential features of the subject matter described herein, nor is it intended to be used as an aid in limiting the scope of the subject matter described herein. Indeed, this disclosure may encompass a variety of aspects that may not be set forth below.

Systems and methods are provided for two dimensional sediment particle shape characterization and paleocurrent direction analysis based on a fullbore image. An example of a method include, receiving, into a processor, a pad borehole image and reconstructing a fullbore image based on the pad borehole image. The method may also include identifying one or more patches that correspond to sediment particles on the fullbore image and computing one or more characteristics for each of the one or more patches. The characteristics may include long/short axis length, size, roundness, sphericity, orientation, or some combination thereof. In some embodiments, the method may also include computing a paleocurrent direction based on the orientation of the one or more patches. Further, the method may include displaying a visual representation of the one or more characteristic, the paleocurrent direction, or some combination thereof.

An example of a system may include a well logging system that conveys a downhole tool into a wellbore of a formation on a cable and a data processing system. The downhole tool may include sensors that obtain image data and the data processing system may include a processor that receives the image data. The processor may identify one or more patches that correspond to sediment particles in the image data and compute one or more characteristics for each of the one or more patches. The characteristics may include long/short axis length, size, roundness, sphericity, orientation, or some combination thereof. In some embodiments, the processor may also compute a paleocurrent direction based on the orientation of the one or more patches. Further, the processor may display a visual representation of the one or more characteristics, the paleocurrent direction, or some combination thereof.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
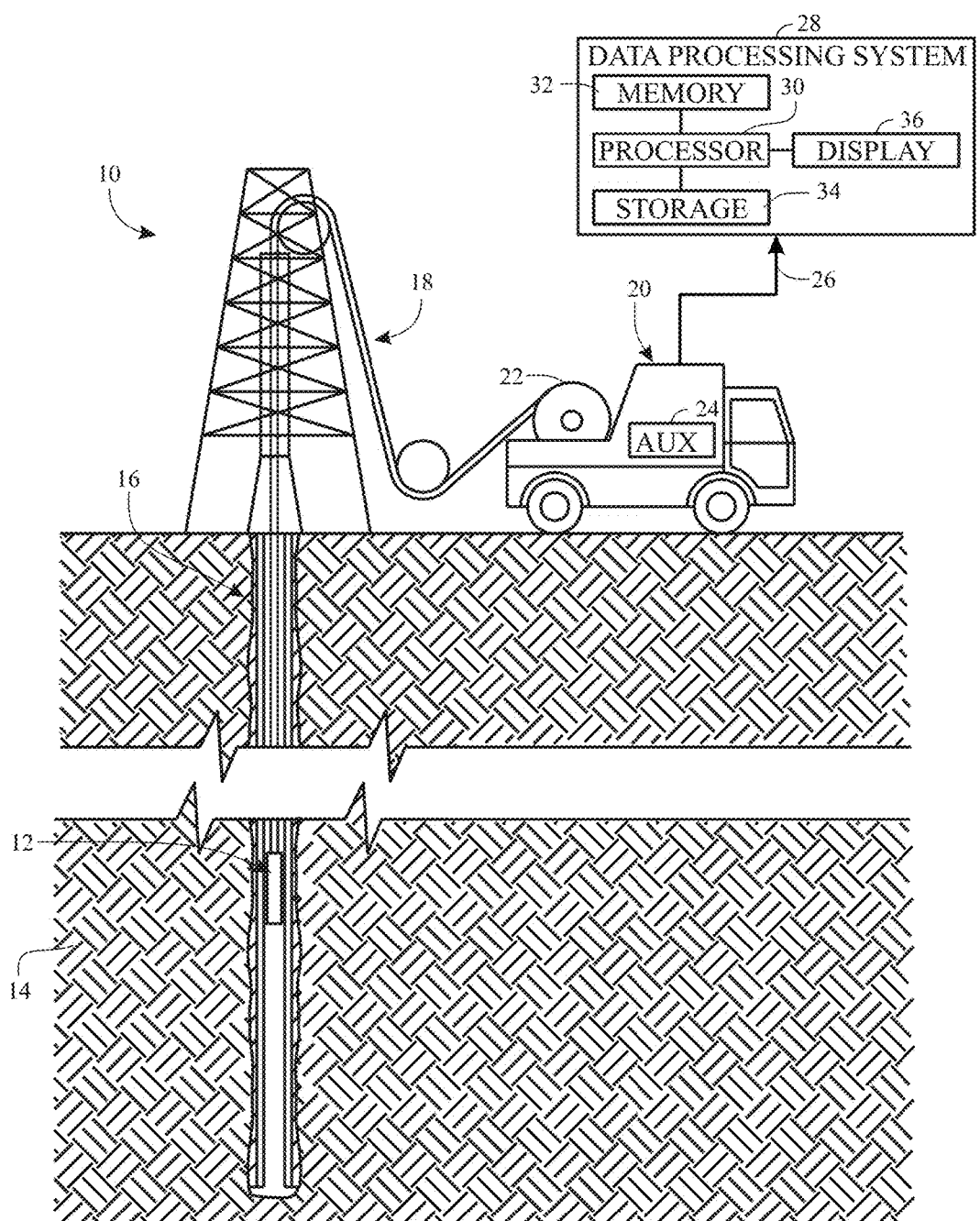
FIG. 1 is a schematic diagram of a well-logging system that employs a logging winch system, in accordance with an embodiment.

One or more specific embodiments of the present disclosure will be described below. These described embodiments are examples of the presently disclosed techniques. Additionally, in an effort to provide a concise description of these embodiments, features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Embodiments of the present disclosure generally relate to performing sediment particle shape and paleocurrent direction analysis using a high resolution fullbore image. Fullbore images are substantially complete, 360-degree views of a borehole wall. It should be understood that "paleo" means at the time of deposit. The disclosed analysis may enable determining certain sediment particle characteristics, such as long/short axis, patches size, roundness, sphericity, and patch orientation, with high accuracy from the fullbore image instead of core data, and provide valuable information for sedimentary analysis along boreholes. Using fullbore image reconstruction technology or an existing fullbore image, heterogeneity and texture of the rocks such as pebble, clasts, vugs on the borehole images may be better visualized. Information provided by the fullbore image obtained from pad images may enable performing particle shape and size analysis to generate continuous sediment particle statistic curve and cumulative representations, as described below. For example, in some embodiments, the patches on the images corresponding to high and low measurement on a reconstructed fullbore image and high definition azimuthal fullbore images are identified and analyzed. The patches are representative of different sizes of sediment particles. Subsequently, the long/short axis length and size of the patches are calculated. In some embodiments, the axis length of a patch on an image may be calibrated with lab measurements on core data. In addition, in some embodiments, the roundness and sphericity of each patch may be computed from geometry analysis of the image. Also, the apparent dip of long axis of patches may be used for paleocurrent direction analysis (e.g., in conglomerate formation when there is a lack of cross bedding evidence).

With this in mind, FIG. 1 illustrates a well-logging system 10 that may employ the formation texture and rock type identification systems and methods of this disclosure. The well-logging system 10 may be used to convey a downhole tool 12 through a geological formation 14 via a wellbore 16. The downhole tool 12 is conveyed on a cable 18 via a logging winch system 20. Although the logging winch system 20 is schematically shown in FIG. 1 as a mobile logging winch system carried by a truck, the logging winch system 20 may be substantially fixed (e.g., a long-term installation that is substantially permanent or modular). Any suitable cable 18 for well logging may be used. The cable 18 may be spooled and unspooled on a drum 22 and an auxiliary power source 24 may provide energy to the logging winch system 20 and/or the downhole tool 12.

Although the downhole tool 12 is described as a wireline downhole tool, it should be appreciated that any suitable conveyance may be used. For example, the downhole tool 12 may instead be conveyed as a logging-while-drilling (LWD) tool as part of a bottom hole assembly (BHA) of a drill string, conveyed on a slickline or via coiled tubing, and so forth. For the purposes of this disclosure, the downhole tool 12 may be any suitable measurement tool that uses electrical sensors to obtain high-resolution measurements of the wellbore 16 wall.

As discussed further below, the downhole tool 12 may include a number of sensors used to acquire data 26 about the wellbore 16 and/or geological formation 14 by taking measurements. For example, the data 26 may be images of the wellbore 16 obtained via sensor pads. The data 26 may be sent to a data processing system 28. The data processing system 28 may analyze the data 26 to reconstruct a high resolution fullbore image used to determine characteristics (e.g., long/short axis, patches size, roundness, sphericity, and patch orientation) of sediment particles identified in the fullbore image, among other things. The data processing system 28 may be any electronic data processing system that can be used to carry out the systems and methods of this disclosure. For example, the data processing system 28 may include a processor 30, which may execute instructions stored in memory 32 and/or storage 34. As such, the memory 32 and/or the storage 34 of the data processing system 28 may be any suitable article of manufacture that can store the instructions. The memory 32 and/or the storage 34 may be ROM memory, random-access memory (RAM), flash memory, an optical storage medium, or a hard disk drive, to name a few examples. A display 36, which may be any suitable electronic display, may display the images generated by the processor 30. The data processing system 28 may be a local component of the logging winch system 20, a remote device that analyzes data from other logging winch systems 20, or partly local and partly remote. In some embodiments, the data processing system 28 may be a mobile computing device (e.g., tablet, smartphone, or laptop) or a server remote from the logging winch system 20.

Figure 2:
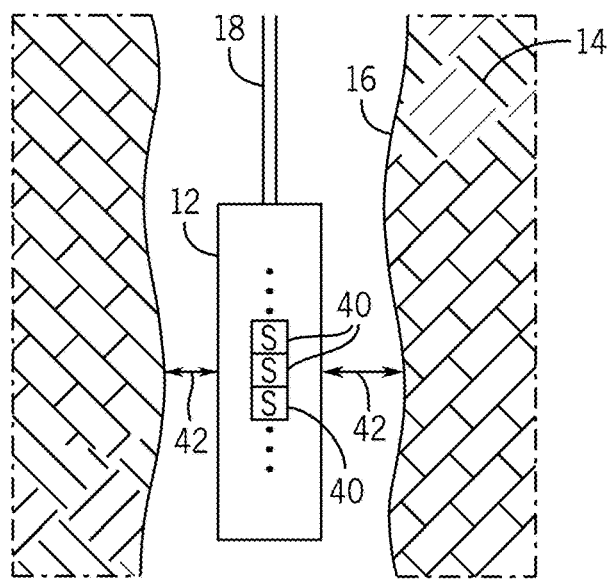
FIG. 2 is a schematic diagram of a downhole tool used by the well-logging system of FIG. 1, in accordance with an embodiment.

FIG. 2 is a schematic diagram of the downhole tool 12 used by the well-logging system 10 of FIG. 1, in accordance with an embodiment. As illustrated, the downhole tool 12 may include a number of sensors 40 that are used to measure characteristics of the formation 14. Each sensor 40 may be referred to as an imaging pad. In some embodiments, any number of imaging pads (e.g., 1, 2, 3, 4, 5, 6, 7, 8, 9, or 10) may be used. In one embodiment, 8 imaging pads may be used. In some embodiments, the imaging pads 40 may be disposed on a respective independent, interlaced trapezoidal dual arm. Each imaging pad 40 may include a number of microelectrodes (e.g., imaging buttons) and one or more current return electrodes. Any suitable number (e.g., 5, 10, 15, 20, 24, 25, or 26) of imaging buttons may be disposed on each imaging pad 40. In one embodiment, 24 imaging buttons may be disposed on a single imaging pad 40. Also, any suitable number (e.g., 1, 2, 3, 4, or 5) of current return electrodes may be disposed on each imaging pad 40. In one embodiment, 2 current return electrodes may be disposed on one imaging pad 40. Accordingly, in one embodiment, the downhole tool 40 may include 8 imaging pads 40, each including 24 imaging buttons for an array of 192 imaging buttons and 2 current return electrodes. In some embodiments, the imaging pads 40 may press against the sidewall of the borehole 16, thus contacting the formation 14. In some embodiments, the imaging pads 40 may not fully cover the circumference of the borehole, resulting in gaps circumferentially spaced apart within the borehole image. The processor 30 may reconstruct a fullbore image by filling in the gaps. In some embodiments, the processor 30 may use techniques similar to those disclosed in Patent Application No. PCT/US2014/041702, which is incorporated by reference herein for all purposes. It should be understood that the arrangement and usage of the imaging pads 40 on the various arms may enable reconstructing high resolution fullbore images.

In some embodiments, to perform measurements, an alternating current (AC) voltage is applied between a current return electrode and the array of imaging buttons. The resulting AC current may pass directly through each imaging button. As such, the downhole tool 12 may be equally sensitive to both vertical and horizontal features of the borehole 16 and/or the geological formation 14. In some embodiments, the current may flow from the imaging button through the borehole OBM and geological formation 14 to the two current return electrodes. The imaging pads 40 may operate in the MHz range, which may reduce the electrical impedance of the OBM, and enable high-resolution images to be generated. The data obtained by the imaging pads 40 may be delivered to the data processing system 28 via a telemetry system that may include the transmissions over the cable 18 or wirelessly.

Figure 3:
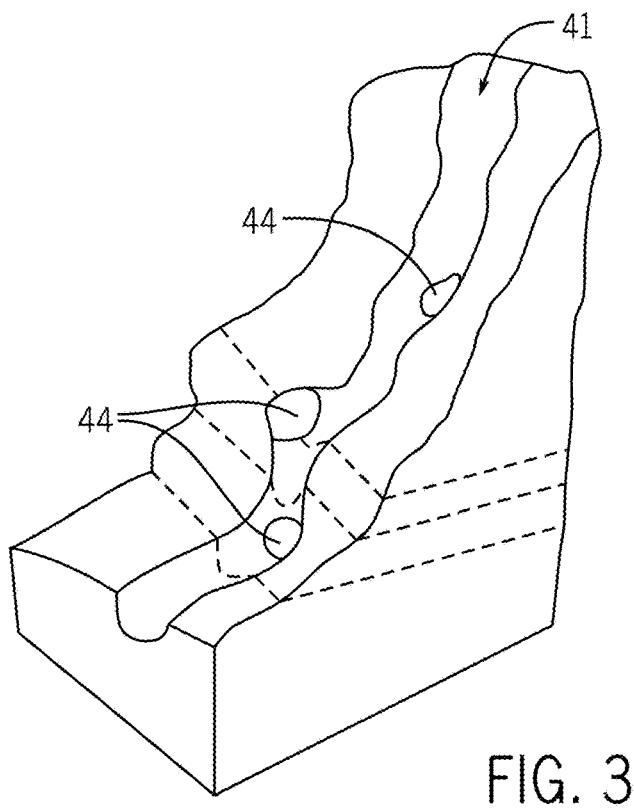
FIG. 3 illustrates sediment laid down millions of years ago in a mountainous stream.

FIG. 3 illustrates sediment 44 laid down millions of years ago in a mountainous stream 41. The sediment 44 may include rocks of any size including pebbles or boulders. As may be appreciated, the sediment 44 and the mountainous stream 41 may currently be buried deep beneath the surface of the earth. However, the borehole 16 may penetrate a portion of the mountainous stream 41 and the downhole tool 12 may be used to locate and analyze the sediment 44 and/or the mountainous stream 41. For example, using the disclosed techniques may enable identifying sediment particles and determining characteristics of those sediment particles. Certain characteristics may indicate that the sediment particles were part of the mountainous stream. In some embodiment, using paleocurrent analysis, the processor 30 may determine an orientation of the sediment, which may indicate a direction of flow of water in the mountainous stream 41. The sediment particle characteristics (e.g., long/short axis, patches size, roundness, sphericity, and patch orientation) may be commercially beneficial to entities engaged in natural resource exploration and recovery.

Figure 4:
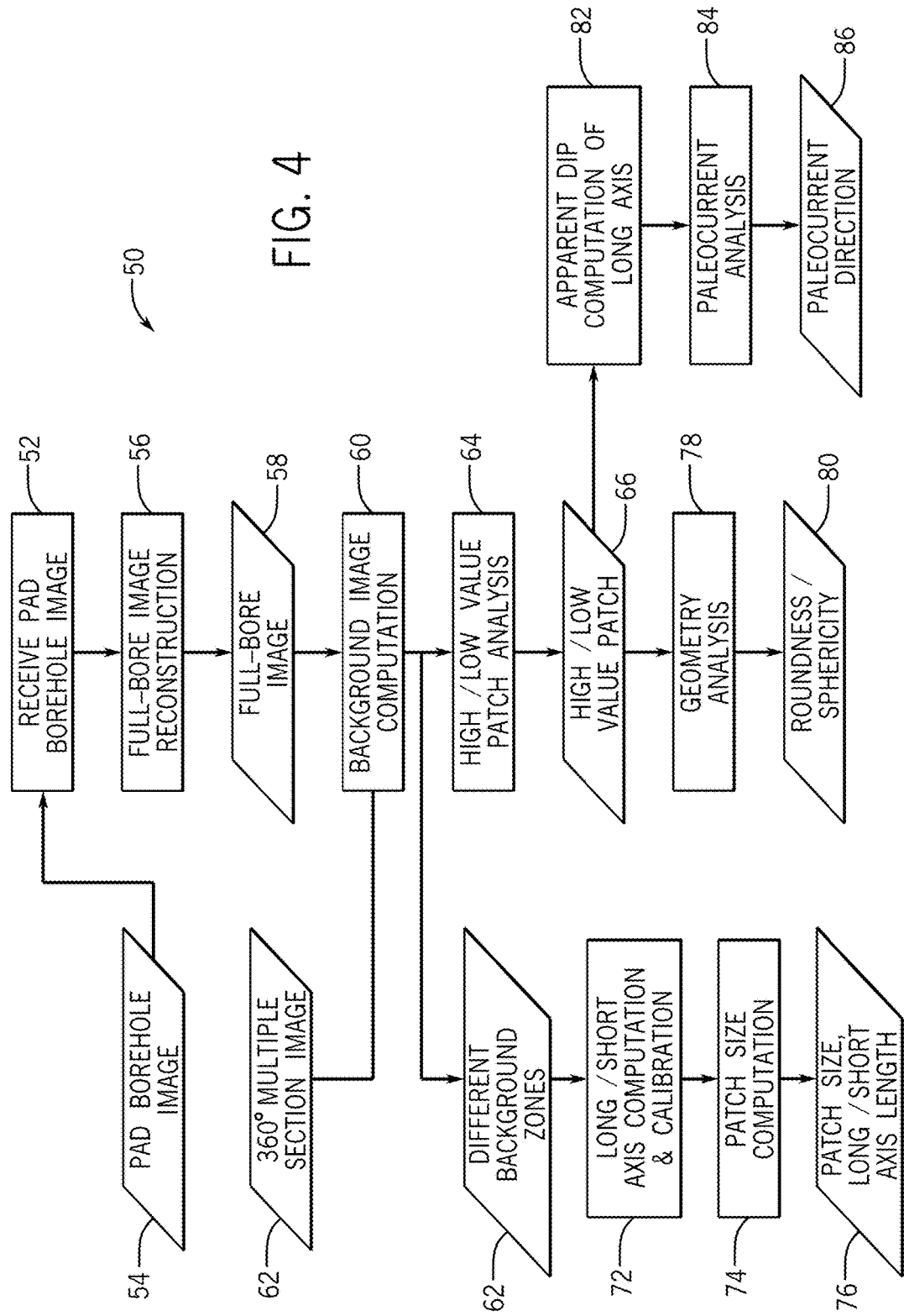
FIG. 4 is a flowchart of a method for sediment particle analysis, in accordance with an embodiment.

FIG. 4 is a flowchart of a method 50 for sediment particle analysis, in accordance with an embodiment. Although the following description of the method 50 is described as being performed by the processor 30 of the data processing system 28, it should be noted that the method 50 may be performed by other processors disposed on other devices that may be capable of communicating with the data processing system 28, such as a computing device or other component associated with the well-logging system 10. Additionally, although the following method 50 describes a number of operations that may be performed, it should be noted that the method 50 may be performed in a variety of suitable orders and some of the operations may not be performed. It should be appreciated that the method 50 may be wholly executed by the data processing system 28 or the execution may be distributed between another computing device (e.g., downhole tool 12) and the data processing system 28. It should be noted that the method 50 may be implemented as computer instructions stored on the memory 38 and/or storage 40.

Referring now to the method 50, the processor 30 may receive (block 52) one or more pad borehole images 54. As discussed above, the pad borehole images 54 may be obtained by the imaging pads 40 of the downhole tool 12 and sent to the data processing system 28 from the downhole tool 12. Further, the pad borehole image may have one or more gaps that correspond to the location of the imaging pads 40 on the borehole wall. Accordingly, the processor 30 may perform (block 56) fullbore image 58 reconstruction to fill in the gaps of the pad borehole image 54. For example, filling in the gaps may include reconstructing one or more trends in the missing regions. Such trends may correspond to low pass information, and may include dips and/or other structured data. One or more of such trends may be generated by a linear combination of the pixels surrounding the gaps. Weighting associated with each pixel may be defined by image gradients, which may improve and/or ensure continuity of the reconstructed data. Given the trend(s), the texture may be estimated in the missing regions.

The processor 30 may compute (block 60) background image based on the reconstructed fullbore image 58 or an existing 360 multiple sections image 62 (e.g., from LWD tool). The existing 360 multiple sections image 62 may be retrieved from the memory 32 and/or storage 34, another communicatively coupled computing device, or the like. The processor 30 may define different background zones 62 for the background image. Further, the processor 30 may perform (block 64) high/low value patch 66 analysis to identify the patches, which may correspond to sediment particles in conglomerate formation. Although the high/low patch analysis is discussed with regards to conglomerate formation, it should be noted that the analysis may be performed for other suitable formations as long as the grains contour and orientation can be determined on the images. It should be noted that the above steps of the method 50 may be referred to as preprocessing steps.

Once the patches have been identified, the processor 30 may determine the sediment particle shape. In some embodiments, two-dimensional (2D) particle shape factors are computed including area, long/short axis, roundness, sphericity, and orientation. The processor 30 may simplify the raw patches identified in the patch analysis. The extracted raw patches are image pixels based and may consist of irregular shapes due to data inconsistency between imaging pads 40 (Wireline tools) or between sectors (LWD tools). In addition, the large amount of points in each patch consumes extensive computational cost. Thus, in some embodiments, these patches are processed by a polygon simplification method, which reduces the number of points, and extracts certain characteristics of the patch for further analysis.

In some embodiments, a polygon simplification method referred to as the Ramer-Douglas-Peucker method (RDP), also known as the iterative endpoint fit method in computational geometry, may be used. This method has an expected complexity of $O(n \log n)$. Although the RDP method is described below, it should be noted that any suitable variant or variation of the procedure, such as modification of the implementation specifics or parallelization which may achieve better performance, may be used. Given a polygon composed of line segments, the RDP method determines a similar curve with far fewer points. "Similar" may refer to the maximum distance between the original curve and the simplified curve. The details of the RDP method are provided below:

The initial polygon contains points between the first and last point. Set a distance threshold ε>0.

The first and last points are marked to be kept. The method searches for the point that is furthest from the line segment joining the first and last point.

If the furthest point has a distance closer than ε to the line segment, then any points not currently marked to be kept may be discarded. If it is greater than ε, then that point is kept.

If the furthest point is kept, the method recursively calls itself with the two split parts: the part between the first point and the furthest point; and the part between the furthest point and the last point.

When the recursion is completed, a new output curve is generated consisting of just those points that have been kept.

Figure 5:
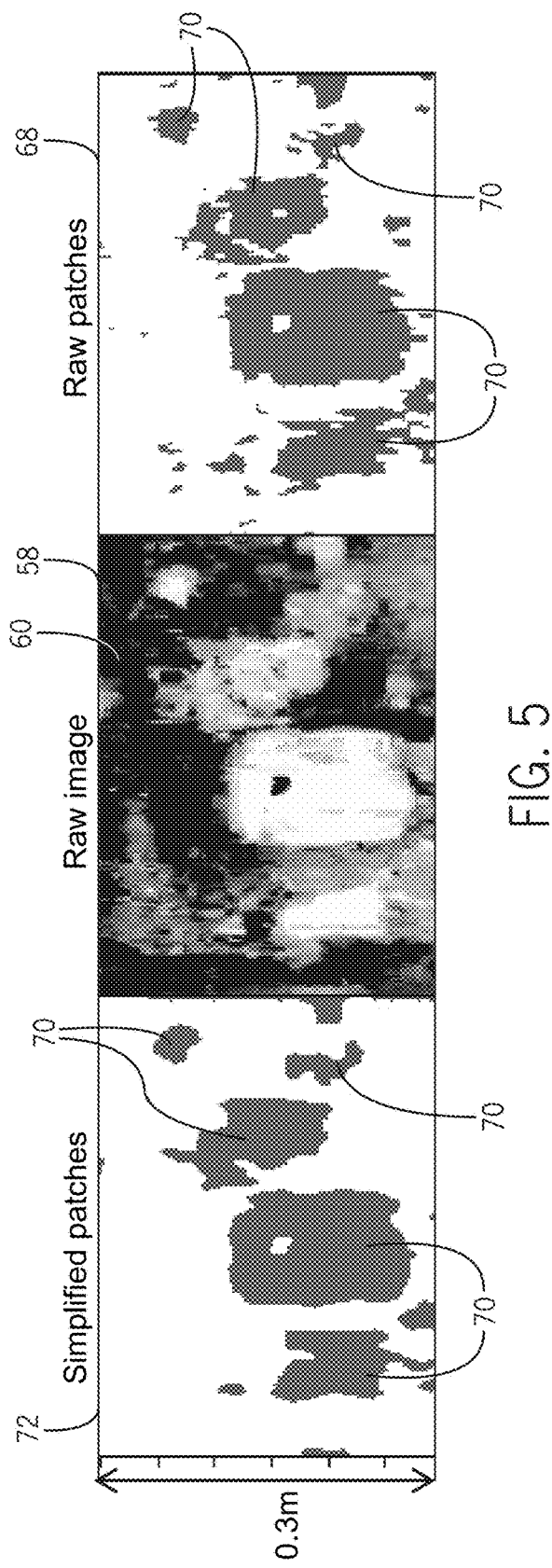
FIG. 5 is an illustration of images associated with patch simplification, in accordance with an embodiment.

An example of polygon simplification of pebble detected on an image is given in FIG. 5. Polygon simplification may significantly reduce the number of points and allows for definition of a clear shape. As depicted, a fullbore image 58 may be reconstructed and the high/low value patches 66 may be identified to generate a raw patches image 68. As depicted in the raw patches image 68, patches 70 are darkly shaded against the light background. The raw patches image 68 may be further processed using the polygon simplification procedure (e.g., RDP method) described above to generate a simplified patches image 72. In the simplified patches image 72, the shapes of the patches 70 are more clearly defined than the shapes of the patches 70 in the raw patches image 68.

Returning to the method 50 of FIG. 4, after patch simplification, the different background zones 62 and the high/low value patches 66 may be used by the processor 30 to perform (block 72) long/short axis computation and calibration. In some embodiments, the minimum bounding rectangle of each polygon is found using a computational geometry method. The orientation and size of the bounding rectangle may be used to determine the apparent long/short axis of the patch. In some embodiments, a O(n log n) complexity convex hull method is used to generate a convex polygon based on the patch polygon. The processor 30 may use a method referred to as "rotating calipers" to compute the minimal area (or minimum perimeter) enclosing rectangle in O(n) time. Details related to finding the minimal area enclosing rectangle for a convex polygon with n vertices given in clockwise order are provided below:

Compute the four extreme points for the polygon.

Construct four lines of support for P through the four points. These determine two sets of "calipers".

If one (or more) lines coincide with an edge, then compute the area of the rectangle determined by the four lines, and keep as minimum. Otherwise, consider the current minimum area to be infinite.

Rotate the lines clockwise until one of them coincides with an edge of its polygon.

Compute the area of the new rectangle, and compare it to the current minimum area. Update the minimum if desired, keeping track of the rectangle determining the minimum.

Repeat steps previous two steps (e.g., rotate the lines and compute the area), until the lines have been rotated an angle greater than 90 degrees.

Output the minimum area enclosing rectangle.

In some embodiments, the processor 30 may calibrate the axis based on contrast between patch and background value by comparing with measurements if they have been done on core data at same depth interval. The processor 30 may also perform (block 74) patch size computation. Accordingly, the processor 30 may compute the area of each extracted patch for further statistical analysis. The area of the patch may be calculated in accordance with the following relationship:

$$\text{Area} = \frac{1}{2} |(x_1 y_2 - x_2 y_1) + (x_2 y_3 - x_3 y_2) + \ldots + (x_n y_1 - x_1 y_n)| \quad \text{Equation (1)}$$

Where $(x_1, y_1), \ldots (x_n, y_n)$ are the N vertices of the non-self-intersecting patch polygon. Once computed, the processor 30 may output the patch size and the long/short axis length 76 to be displayed, send the patch size and long/short axis length to another computing device, or the like.

Further, the high/low value patches 66 may be used by the processor 30 to perform (block 78) geometry analysis that results in roundness and sphericity of the patches 80. Roundness may refer to the degree of smoothing due to abrasion of sedimentary particles. Roundness is expressed as the ratio of the average radius of curvature of the edges or corners to the radius of curvature of the maximum inscribed sphere. For practical purpose there can be, for example, up to six categories of roundness: very angular, angular, sub-angular, sub-rounded, rounded, and well-rounded. For a polygon patch, the numerical formula for computing roundness is calculated in accordance with the following relationship:

$$\text{Roundness} = \frac{\sum_{0}^{n}(r_i/R)}{N} \quad \text{Equation (2)}$$

Where $r_i$ are the individual radii of corners of a patch, N is the number of corners, and R is the radius of maximum inscribed circle. The corresponding ranges of six categories may be defined from 0 to 6 using equation (2).

Sphericity may be computed on the particle projection in two dimensions which may also be referred to as circularity. Sphericity may be computed in accordance with the following relationship:

$$\text{Sphericity} = \frac{4\pi \text{Area}}{\text{Perimeter}^2} \quad \text{Equation (3)}$$

Where Area is computed using equation 1 and Perimeter is the length of the perimeter of the patch. If the computed roundness is greater than 0.9, the patch is very close to circular in shape.

In addition, the processor 30 may use the high/low value patches 66 to perform (block 82) apparent dip computation for long axis of each patch. In some embodiments, the processor 30 may automatically correct the azimuth for the long axis for paleocurrent analysis (block 84) because long axis is inclined to upstream direction. The paleocurrent analysis (block 84) results in a paleocurrent direction 86.

Figure 6:
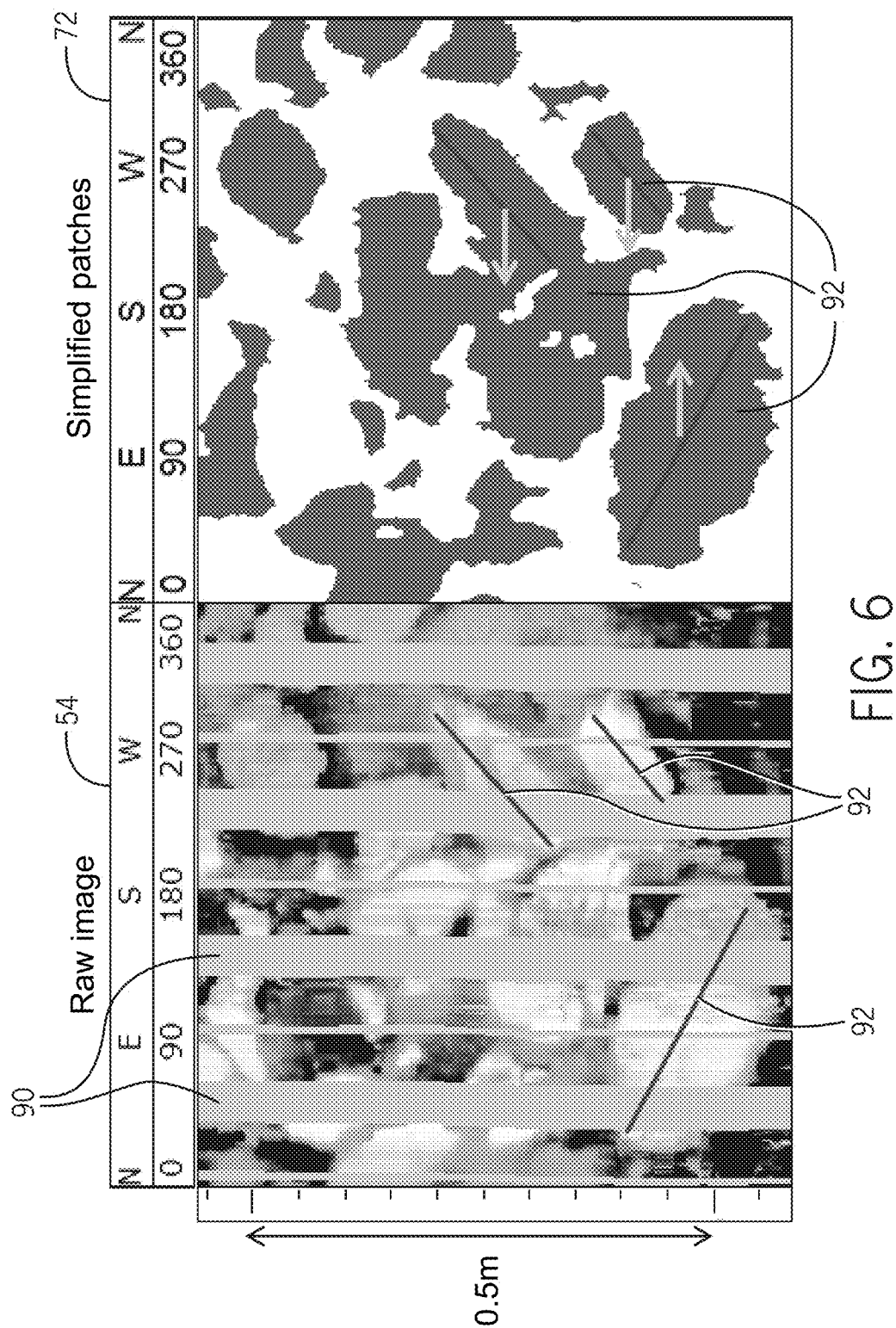
FIG. 6 is an illustration of azimuth correction for the long axis used in paleocurrent analysis, in accordance with an embodiment.

An example azimuth correction for the long axis 92 for paleocurrent analysis (block 84) is shown in FIG. 6, in accordance with an embodiment. As depicted, a pad borehole image 54 that includes gaps 90 is initially received by the processor 30. After filling in the gaps 90 and simplifying the patches, the azimuth is corrected for the long axis 92.

Figure 7:
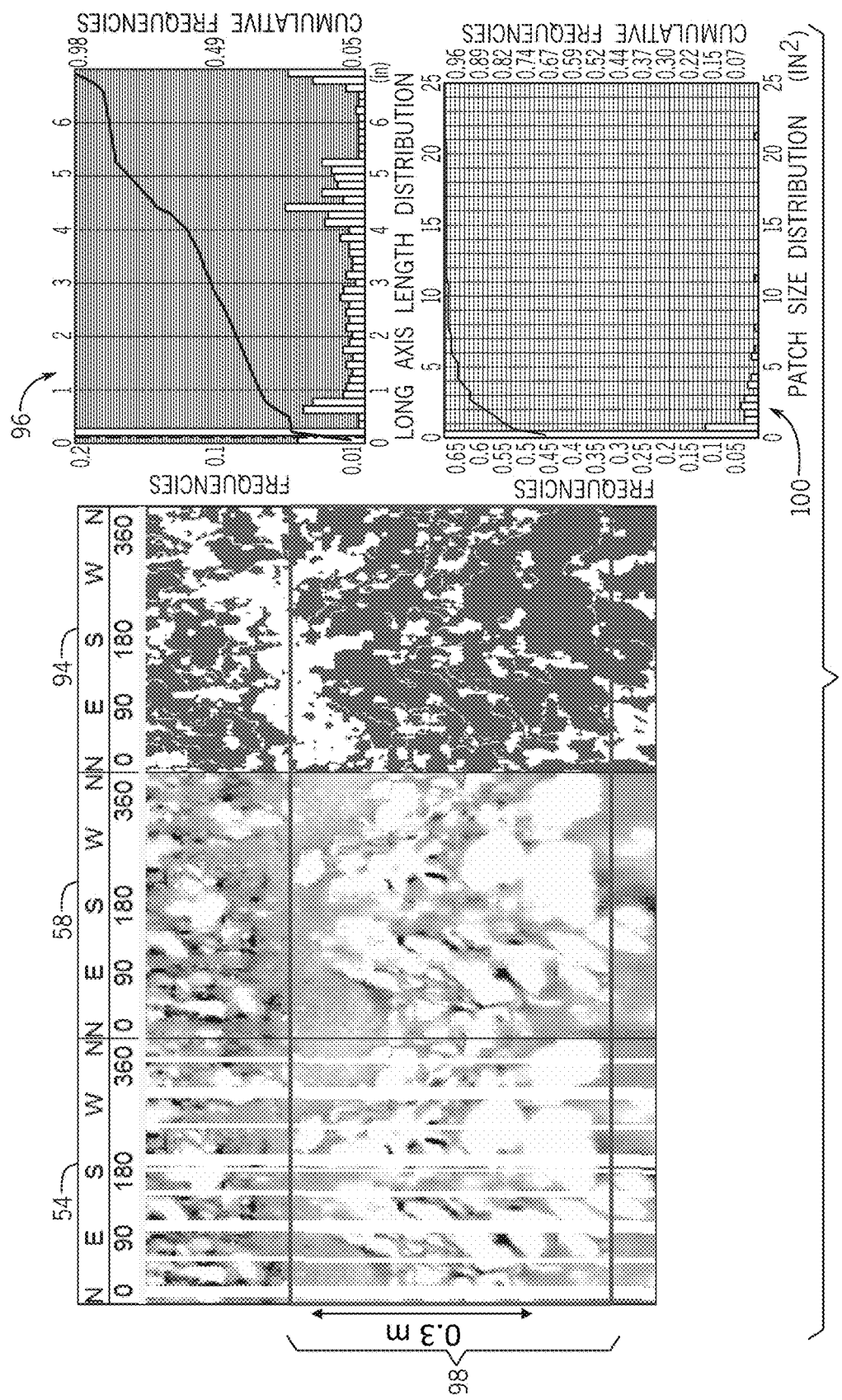
FIG. 7 is an illustration of patch size distribution and axis length distribution in a defined zone, in accordance with an embodiment.
Figure 8:
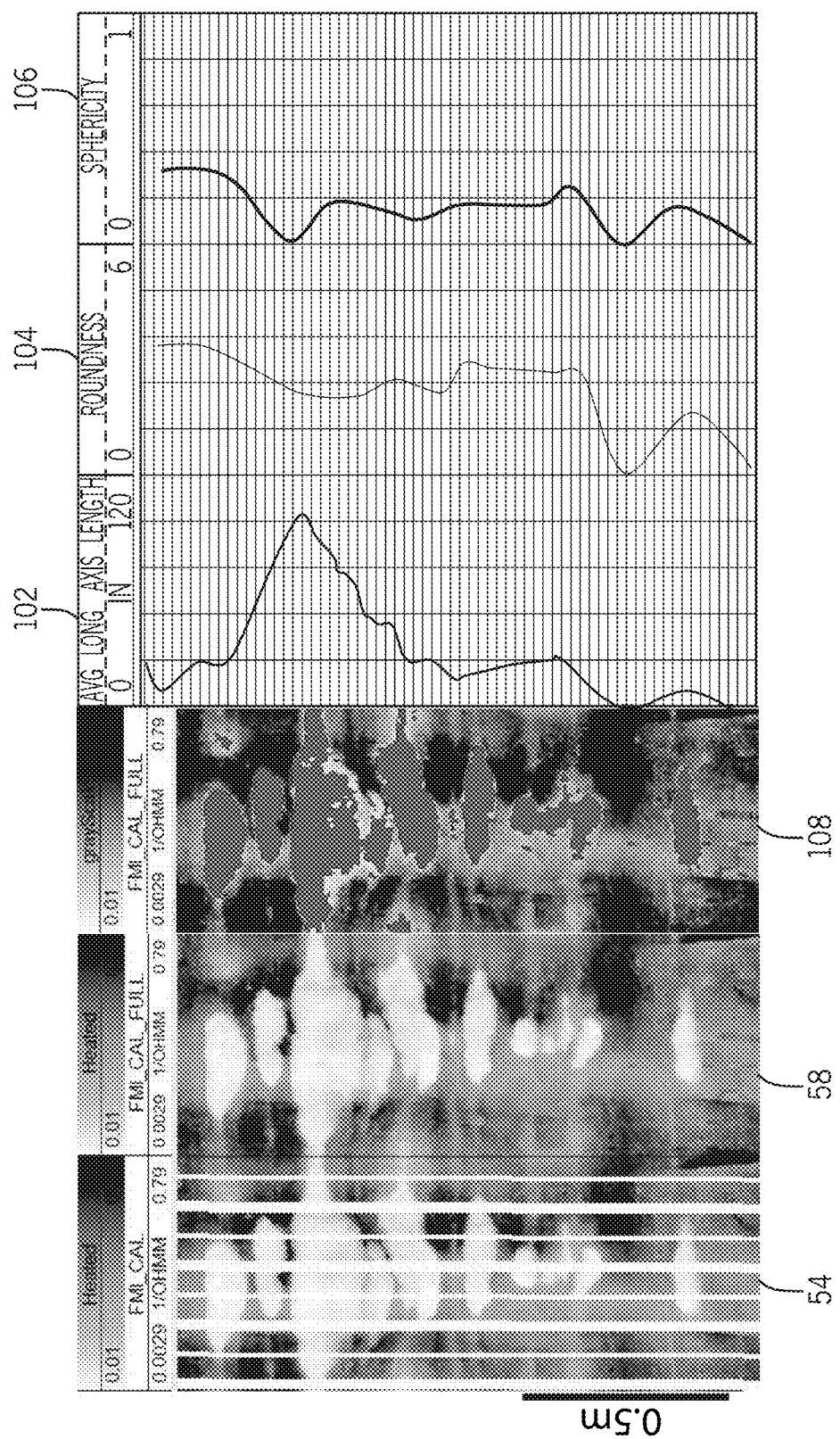
FIG. 8 is an illustration of continuous curves of average long axis length, average roundness, and sphericity, in accordance with an embodiment.
Figure 9:
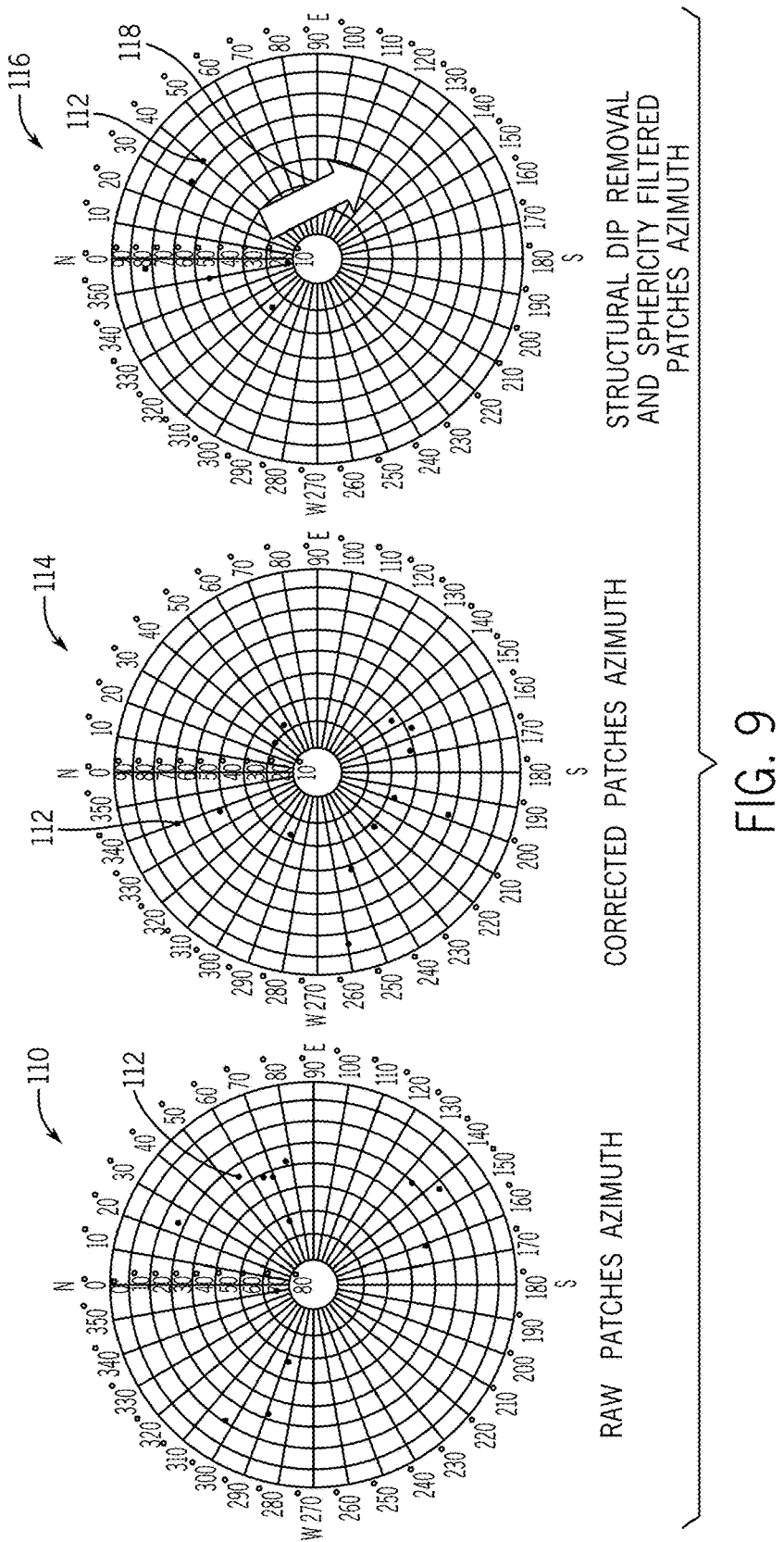
FIG. 9 is an illustration of stereonets associated with paleocurrent analysis from corrected azimuth statistic with structural dip removal and sphericity filtering, in accordance with an embodiment.

The results of the method 50 may include the following outputs to describe the paleo-dynamics: zonal patch size distribution and axis length distribution (FIG. 7); continuous curves of average axis length, average roundness, and sphericity for each zone (FIG. 8); and paleocurrent direction analysis in stereonet window or dip vector plot with sphericity filtering and structural dip removal (FIG. 9). The outputs may be displayed as visual representations. Starting with FIG. 7, the processor 30 receives the pad borehole image 54 with gaps and reconstructs a fullbore image 58 with the gaps filled in. As depicted, the processor 30 may perform background image computation (block 60), high/low value patch analysis (block 64), and/or patch simplification to generate a simplified patches image 94. The processor 30 may use the simplified patches image 94 to determine the long axis length for each patch in a defined zone 98 by finding the minimum bounding rectangle of each polygon using computation geometry method, as described above. A graph 96 may be generated that represents the distribution of long axis lengths as frequencies versus long axis length (inches). Further, as discussed above, the size of the patches may be computed by calculating the area of each patch in the defined zone 98. A graph 100 may be generated that represents the patch size distribution as frequency versus size (inches$^2$).

FIG. 8 is an illustration of continuous curves of average axis length (curve 102), average roundness (curve 104), and sphericity (curve 106), in accordance with an embodiment. The processor 30 receives the pad borehole image 54 with gaps and reconstructs the fullbore image 58 by filling in the gaps. The processor 30 may perform patch simplification, background image computation (block 60), and/or high/low value patch analysis (block 64) to generate a simplified patch image 108. Using the simplified patch image 108, the processor 30 may determine the long axis lengths, as discussed above, to generate the continuous curve 102 that represents the average long axis length for the patches represented in the simplified patches image 108. Also, the processor 30 may compute the roundness and sphericity for each of the patches represented in the simplified patches image 108 and generate the continuous curves 104 and 106 for roundness and sphericity, respectively.

FIG. 9 is an illustration of stereonets associated with paleocurrent analysis from corrected azimuth statistics with structural dip removal and sphericity filtering, in accordance with an embodiment. As may be appreciated, when sediment are initially deposited they usually form accumulating deposits much like a layer cake and the resulting sediment is horizontal on a flat surface. Over time, various forces (e.g., physical or hydro pressure) cause the sediment to deform. For example, when a plane of the sediment crosses the borehole 16 at an angle, it has an ovular shape, representing that the sediment is no longer on a horizontal surface like it was when it was deposited. However, if the sediment crosses the borehole 16 horizontally, then it has a circular shape and is in the same orientation that it was at the time of deposit. If the image shows that the sediment (e.g., patches) are at an angle, the processor 30 may rotate the patches until the patches are deposited on a flat surface (e.g., horizontal with circular shape) in the image with the structural dip computed from underlying shale formation. As previously noted, the apparent dip of the long axis indicates the angular degree of slanting. It should be noted that the dots represented in the various stereonets are from the same plane but have different geometries.

A raw patches azimuth stereonet 110 shows the patches that cross the plane intersected by the borehole 16 represented in the image. Dots 112 represent the various patches and their placement on the stereonet 110 indicates their angular location in the borehole 16. A corrected patches azimuth stereonet 114 is generated after the corrected azimuth for the long axis is assigned because the long axis is inclined to upstream direction. Then, a structural removal and sphericity filtered patches azimuth stereonet 116 is generated from the correct patches azimuth stereonet 114. The processor 30 may rotate the dip that was computed for the long axis of each of the patches with the structural dip calculated from the underlying shale formation. The patches 112 shown in the structural removal and sphericity filtered patches azimuth stereonet 116 represent the patches deposited on a flat surface in the plane captured by the image. From this stereonet 116, a paleocurrent direction (arrow 118) may be determined. In some embodiments, the paleocurrent direction may be a number value.

The specific embodiments described above have been shown by way of example, and it should be understood that these embodiments may be susceptible to various modifications and alternative forms. It should be further understood that the claims are not intended to be limited to the particular forms discloses, but rather to cover modifications, equivalents, and alternatives falling within the spirit of this disclosure.

The invention claimed is:

1. A method comprising:
   obtaining, via a processor, a borehole image derived from a downhole tool in a wellbore of a geological formation;
   identifying, via the processor, one or more patches that correspond to sediment particles on the borehole image;
   computing, via the processor, one or more characteristics for each of the one or more patches, wherein the one or more characteristics comprise long/short axis length, size, roundness, sphericity, orientation, or some combination thereof;
   displaying a visual representation for each of the one or more characteristics; and
   computing, via the processor, a paleocurrent direction based at least in part on the orientation of the one or more patches.

2. The method of claim 1, wherein computing the paleocurrent direction comprises filtering sphericity and removing structural dip from the one or more patches.

3. The method of claim 1, wherein the visual representation of the one or more characteristics comprises a stereonet or dip vector plot of the paleocurrent direction.

4. The method of claim 1, wherein the visual representation of the one or more characteristics comprises:
   a zonal patch size distribution and axis length distribution;
   continuous curves for average axis length, average roundness, average sphericity;
   or some combination thereof.

5. The method of claim 1, wherein the borehole image comprises a reconstructed fullbore image or a 360° multiple section image.

6. The method claim 1, comprising performing polygon simplification for each of the one or more patches to reduce the number of points included in each of the one or more patches prior to computing the one or more characteristics.

7. The method of claim 1, wherein computing the long/short axis length for each of the one or more patches comprises determining a minimum bounding rectangle of each polygon of each of the one or more patches and an orientation and size of the bounding rectangle is used to compute the long/short axis length.

8. The method of claim 1, wherein computing the size for each of the one or more patches comprises computing an area of each of the one or more patches in accordance with the following relationship:

$$\text{Area} = \frac{1}{2}|(x_1 y_2 \, x_2 y_1) + (x_2 y_3 \, x_3 y_2) + \ldots + (x_n y_1 \, x_1 y_n)|$$

where $(x_1, y_1), \ldots (X_n, Y_n)$ are the number of vertices of a non-self-intersecting patch polygon of the one or more patches.

9. The method of claim 8, wherein the sphericity of each of the one or more patches is computed in accordance with the following relationship:

$$\text{Sphericity} = \frac{4\pi \text{Area}}{\text{Perimeter}^2},$$

where Area is the area of the patch and Perimeter is the length of the perimeter of the patch.

10. The method of claim 1, wherein the roundness of each of the one or more patches is computed in accordance with the following relationship:

$$\text{Roundness} = \frac{\sum_{0}^{n}(r_i/R)}{N},$$

where $r_i$ are individual radii of corners of a patch, N is the number of corners, and R is the radius of maximum inscribed circle.

11. The method of claim 1, wherein each of the one or more patches corresponds to a group of the sediment particles of similar size.

12. A system, comprising:
a downhole tool; and
a data processing system comprising a processor configured to:
receive image data of a borehole wall from the downhole tool;
identify one or more patches that correspond to sediment particles on the image data;
compute one or more characteristics for each of the one or more patches, wherein the characteristics comprise long/short axis length, size, roundness, sphericity, orientation, or some combination thereof;
compute a paleocurrent direction based on the orientation of the one or more patches; and
display a visual representation of the one or more characteristics, the paleocurrent direction, or some combination thereof.

13. The system of claim 12, wherein the downhole tool comprises a wireline tool or a logging while drilling tool.

14. The system of claim 12, wherein the processor is configured to reconstruct a fullbore image of the borehole wall using the image data prior to identifying the one or more patches.

15. The system of claim 14, wherein the processor is configured to compute the paleocurrent direction by computing an apparent dip for a long axis of each of the one or more patches and removing the apparent dip from the one or more patches.

16. The system of claim 12, wherein the visual representation of the one or more characteristics comprises:
a zonal patch size distribution and axis length distribution;
continuous curves for average axis length, average roundness, average sphericity, or some combination thereof;
a stereonet comprising the paleocurrent direction and the one or more patches relative to their angular location; or
some combination thereof.

17. The system of claim 12, wherein the processor is configured to calibrate the axis for each of the one or more patches based on contrast between each of the one or more patches and a background value by comparing with measurements from a core sample at the same depth interval.

18. A tangible, non-transitory computer-readable medium storing instructions that, when executed by a processor, cause the processor to:
receive a pad borehole image;
reconstruct a fullbore image based on the pad borehole image;
identify one or more patches that correspond to sediment particles on the fullbore image;
perform polygon simplification for each of the one or more patches;
compute one or more characteristics for each of the one or more patches, wherein the characteristics comprise long/short axis length, size, roundness, sphericity, orientation, or some combination thereof;
display a visual representation of the one or more characteristics; and
compute a paleocurrent direction based at least in part on the orientation of the one or more patches.

19. The computer-readable medium of claim 18, wherein the instructions, when executed by the processor, cause the processor to compute the paleocurrent direction based on an azimuthal correction corresponding to the orientation of the one or more patches.

* * * * *